(12) United States Patent
Conrad et al.

(10) Patent No.: US 7,879,747 B2
(45) Date of Patent: Feb. 1, 2011

(54) ELASTIC LAMINATES HAVING FRAGRANCE RELEASING PROPERTIES AND METHODS OF MAKING THE SAME

(75) Inventors: John H. Conrad, Alpharetta, GA (US); Patrick Payne, Lithonia, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 499 days.

(21) Appl. No.: 11/694,190

(22) Filed: Mar. 30, 2007

(65) Prior Publication Data

US 2008/0241541 A1    Oct. 2, 2008

(51) Int. Cl.
B32B 5/16      (2006.01)
B32B 37/00     (2006.01)
A61F 13/15     (2006.01)

(52) U.S. Cl. .................. 442/417; 442/328; 442/329; 442/394; 428/323; 428/327; 428/402.2; 156/145; 604/385.01; 604/385.24; 604/385.25; 604/385.26; 604/385.3

(58) Field of Classification Search ............ None
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,354,506 A | 11/1967 | Raley | |
| 3,494,821 A | 2/1970 | Evans | |
| 3,502,538 A | 3/1970 | Petersen | |
| 3,502,763 A | 3/1970 | Hartman | |
| 3,505,432 A | 4/1970 | Neuwald | |
| 3,516,941 A | 6/1970 | Watson | |
| 3,542,615 A | 11/1970 | Dobo et al. | |
| 3,585,998 A * | 6/1971 | Hayford et al. | ............. 604/359 |
| 3,650,649 A | 3/1972 | Schippers et al. | |
| 3,692,618 A | 9/1972 | Dorschner et al. | |
| 3,801,429 A | 4/1974 | Schrenk et al. | |
| 3,802,817 A | 4/1974 | Matsuki et al. | |
| 3,849,241 A | 11/1974 | Butin et al. | |
| 4,041,203 A | 8/1977 | Brock et al. | |
| 4,087,376 A | 5/1978 | Foris et al. | |
| 4,144,370 A | 3/1979 | Boulton | |
| 4,340,563 A | 7/1982 | Appel et al. | |

(Continued)

FOREIGN PATENT DOCUMENTS

DE    19830308 A1 *   1/2000

(Continued)

OTHER PUBLICATIONS

Abstract of JP 1004237 published Jan. 9, 1989.

(Continued)

*Primary Examiner*—Jennifer A Chriss
(74) *Attorney, Agent, or Firm*—Dority & Manning, P.A.

(57) ABSTRACT

An elastic laminate having fragrance releasing microcapsules embedded within a nonwoven web layer of the laminate is generally disclosed. The elastic laminate is configured to release the encapsulated fragrance upon stretching the laminate. The elastic laminate can continue to release fresh fragrance even after the first stretching force is applied, effectively extending the life of the elastic laminate. The resulting elastic laminate is useful for many applications, and is particularly useful in the construction of an absorbent article.

24 Claims, 6 Drawing Sheets

U.S. PATENT DOCUMENTS

| | | |
|---|---|---|
| 4,374,888 A | 2/1983 | Bornslaeger |
| 4,409,156 A | 10/1983 | Hoshi et al. |
| 4,493,869 A | 1/1985 | Sweeny et al. |
| 4,528,226 A | 7/1985 | Sweeny |
| 4,654,256 A | 3/1987 | Doree et al. |
| 4,663,220 A | 5/1987 | Wisenski et al. |
| 4,713,291 A | 12/1987 | Saski et al. |
| 4,766,029 A | 8/1988 | Brock et al. |
| 4,789,592 A | 12/1988 | Taniguchi et al. |
| 4,795,668 A | 1/1989 | Krueger et al. |
| 4,798,603 A | 1/1989 | Meyer et al. |
| 4,808,408 A | 2/1989 | Baker et al. |
| 4,886,512 A | 12/1989 | Damico et al. |
| 4,908,252 A | 3/1990 | Carnahan et al. |
| 4,937,299 A | 6/1990 | Ewen et al. |
| 4,965,122 A | 10/1990 | Morman |
| 4,981,747 A | 1/1991 | Morman |
| 5,043,161 A | 8/1991 | Scorpelli et al. |
| 5,057,368 A | 10/1991 | Largman et al. |
| 5,069,970 A | 12/1991 | Largman et al. |
| 5,085,514 A | 2/1992 | Mallik et al. |
| 5,108,820 A | 4/1992 | Kaneko et al. |
| 5,162,074 A | 11/1992 | Hills |
| 5,164,046 A | 11/1992 | Ampulski et al. |
| 5,169,706 A | 12/1992 | Collier, IV et al. |
| 5,176,668 A | 1/1993 | Bernardin |
| 5,176,672 A | 1/1993 | Bruemmer et al. |
| 5,180,637 A | 1/1993 | Sumii |
| 5,192,606 A | 3/1993 | Proxmier et al. |
| 5,213,881 A | 5/1993 | Timmons et al. |
| 5,218,071 A | 6/1993 | Tsutsui et al. |
| 5,226,992 A | 7/1993 | Morman |
| 5,272,236 A | 12/1993 | Lai et al. |
| 5,277,976 A | 1/1994 | Hogle et al. |
| 5,278,272 A | 1/1994 | Lai et al. |
| 5,284,703 A | 2/1994 | Everhart et al. |
| 5,322,728 A | 6/1994 | Davey et al. |
| 5,332,613 A | 7/1994 | Taylor et al. |
| 5,336,545 A | 8/1994 | Morman |
| 5,336,552 A | 8/1994 | Strack et al. |
| 5,382,400 A | 1/1995 | Pike et al. |
| 5,385,775 A | 1/1995 | Wright |
| 5,464,688 A | 11/1995 | Timmons et al. |
| 5,466,410 A | 11/1995 | Hills |
| 5,509,915 A | 4/1996 | Hanson et al. |
| 5,539,056 A | 7/1996 | Yang et al. |
| 5,558,659 A | 9/1996 | Sherrod et al. |
| 5,571,619 A | 11/1996 | McAlpin et al. |
| 5,580,578 A | 12/1996 | Oshlack et al. |
| 5,591,146 A | 1/1997 | Hasse |
| 5,596,052 A | 1/1997 | Resconi et al. |
| 5,620,788 A | 4/1997 | Garavaglia et al. |
| 5,649,916 A | 7/1997 | DiPalma et al. |
| 5,733,272 A | 3/1998 | Brunner et al. |
| 5,746,776 A | 5/1998 | Smith et al. |
| 5,800,897 A | 9/1998 | Sharma et al. |
| 5,804,264 A | 9/1998 | Bowen |
| 5,827,913 A | 10/1998 | Baetzold et al. |
| 5,922,406 A | 7/1999 | Ludford, III |
| 5,928,661 A | 7/1999 | Fujita et al. |
| 5,932,497 A | 8/1999 | Morman et al. |
| 5,951,534 A * | 9/1999 | Cummings et al. .......... 604/359 |
| 5,972,041 A | 10/1999 | Smith et al. |
| 5,997,586 A | 12/1999 | Smith et al. |
| 5,997,981 A | 12/1999 | McCormack et al. |
| 6,015,764 A | 1/2000 | McCormack et al. |
| 6,045,833 A | 4/2000 | Landau |
| 6,063,365 A | 5/2000 | Shefer et al. |
| 6,110,158 A | 8/2000 | Kielpikowski |
| 6,111,163 A | 8/2000 | McCormack et al. |
| 6,200,669 B1 | 3/2001 | Marmon et al. |
| 6,213,409 B1 | 4/2001 | Warren et al. |
| 6,231,719 B1 | 5/2001 | Garvey et al. |
| 6,261,483 B1 | 7/2001 | Frank et al. |
| 6,291,371 B1 | 9/2001 | Shefer et al. |
| 6,299,729 B1 | 10/2001 | Heath et al. |
| 6,315,864 B2 | 11/2001 | Anderson et al. |
| 6,329,057 B1 | 12/2001 | Dungworth et al. |
| 6,346,297 B2 | 2/2002 | Mullen |
| 6,375,983 B1 | 4/2002 | Kantor |
| 6,426,055 B1 | 7/2002 | Shefer et al. |
| 6,426,325 B1 | 7/2002 | Dente et al. |
| 6,461,457 B1 | 10/2002 | Taylor et al. |
| 6,500,444 B1 | 12/2002 | Ferenc et al. |
| 6,500,563 B1 | 12/2002 | Datta et al. |
| 6,511,465 B1 | 1/2003 | Feiburger et al. |
| 6,524,494 B2 | 2/2003 | Hart et al. |
| 6,607,783 B1 | 8/2003 | Vander Heiden et al. |
| 6,653,524 B2 | 11/2003 | DeLucia et al. |
| 6,663,611 B2 | 12/2003 | Blaney et al. |
| 6,703,011 B2 | 3/2004 | Shefer et al. |
| 6,723,671 B2 | 4/2004 | Zolotarsky et al. |
| 6,774,069 B2 | 8/2004 | Zhou et al. |
| 6,797,116 B2 | 9/2004 | Capizzi |
| 6,806,213 B2 | 10/2004 | Brooks |
| 6,888,044 B2 | 5/2005 | Fell et al. |
| 6,932,982 B2 | 8/2005 | McIver et al. |
| 7,487,554 B1 * | 2/2009 | Epstein et al. ............. 2/209.13 |
| 2001/0046510 A1 | 11/2001 | Mullen |
| 2002/0146489 A1 | 10/2002 | Thoman et al. |
| 2002/0193484 A1 | 12/2002 | Albee |
| 2003/0068951 A1 | 4/2003 | Boggs et al. |
| 2003/0086815 A1 | 5/2003 | Wesley |
| 2003/0122371 A1 | 7/2003 | Rochford et al. |
| 2003/0198673 A1 | 10/2003 | Oshlack et al. |
| 2003/0198680 A1 | 10/2003 | Shefer et al. |
| 2003/0207632 A1 | 11/2003 | Brooks |
| 2003/0222374 A1 | 12/2003 | Castellari |
| 2004/0060112 A1 | 4/2004 | Fell et al. |
| 2004/0121687 A1 | 6/2004 | Morman et al. |
| 2004/0122387 A1 | 6/2004 | Long |
| 2004/0127866 A1 | 7/2004 | Odorzynski |
| 2004/0180044 A1 | 9/2004 | Chao et al. |
| 2004/0220074 A1 | 11/2004 | Fehr et al. |
| 2004/0235705 A1 | 11/2004 | Popplewell et al. |
| 2005/0002996 A1 | 1/2005 | Sojka |
| 2005/0003996 A1 | 1/2005 | Santos et al. |
| 2005/0037056 A1 | 2/2005 | Su |
| 2005/0043209 A1 | 2/2005 | Schmiedel et al. |
| 2005/0129759 A1 | 6/2005 | Sojka |
| 2005/0169813 A1 | 8/2005 | D'Amico et al. |
| 2005/0170729 A1 | 8/2005 | Stadelman et al. |
| 2005/0176598 A1 | 8/2005 | Bergquist et al. |
| 2005/0176599 A1 | 8/2005 | Bergquist et al. |
| 2005/0226900 A1 | 10/2005 | Winton Brooks et al. |
| 2005/0245162 A1 | 11/2005 | McCormack et al. |
| 2005/0260905 A1 | 11/2005 | Buschmann |
| 2007/0014993 A1 | 1/2007 | Longmoore |
| 2007/0049894 A1 | 3/2007 | Fitts, Jr. et al. |

FOREIGN PATENT DOCUMENTS

| | | |
|---|---|---|
| EP | 0387411 | 9/1990 |
| EP | 0392608 | 10/1990 |
| EP | 0630646 | 12/1994 |
| EP | 1367152 | 12/2003 |
| EP | 1384682 | 1/2004 |
| EP | 1443058 | 8/2004 |
| GB | 2198062 | 6/1988 |
| WO | WO 9427646 A1 | 12/1994 |
| WO | WO 9725955 A2 | 7/1997 |
| WO | WO 9725955 A3 | 7/1997 |
| WO | WO 9823149 A1 * | 6/1998 |
| WO | WO 9851248 A1 | 11/1998 |

| | | |
|---|---|---|
| WO | WO 0173188 | 10/2001 |
| WO | WO 2005042603 | 5/2005 |
| WO | WO 2005044381 | 5/2005 |

OTHER PUBLICATIONS

Abstract of JP 1272875 published Oct. 31, 1989.
Abstract of JP 2182980 published Jul. 17, 1990.
Abstract of JP 2200876 published Aug. 9, 1990.
Abstract of JP 3260156 published Nov. 20, 1991.
Abstract of JP 4263893 published Sep. 18, 1992.
Abstract of JP 5163676 published Jun. 29, 1993.
Abstract of JP 6116871 published Apr. 26, 1994.
Abstract of JP 6200459 published Jul. 19, 1994.
Abstract of JP 8026958 published Jan. 30, 1996.
Abstract of JP 9158027 published Jun. 17, 1997.
Abstract of JP 2000144169 published May 26, 2000.
Abstract of JP 2000189734 published Jul. 11, 2000.
Abstract of JP 2003113092 published Apr. 18, 2003.
Abstract of JP 59073923 published Apr. 26, 1984.
Abstract of JP 59124941 published Jul. 19, 1984.
Abstract of JP 60249961 published Dec. 10, 1985.
Abstract of JP 61063716 published Apr. 1, 1986.
Abstract of WO 03101417 published Dec. 11, 2003.
Search Report and Written Opinion for PCT/IB2008/050402 dated Jul. 9, 2008, 13 pages.

* cited by examiner

ELASTIC LAMINATES HAVING FRAGRANCE RELEASING PROPERTIES AND METHODS OF MAKING THE SAME

BACKGROUND OF THE INVENTION

Fragrance releasing microcapsules have been conventionally incorporated into materials for a variety of reasons. Their use in absorbent materials has been directed to the release of fragrance upon applying pressure or wetting. Additionally, fragrance releasing microcapsules have been used as a coating on stretchable articles. In these materials, the fragrance releasing microcapsules have been applied to a surface of the article, and are not positioned within the article's interior construction. For example, when the article is a nonwoven web, the microcapsules have been applied as a layer on one surface of the web, but not having a substantial amount of microcapsules, if any, within the web's interior fiber structure.

Once the external force (e.g., pressure, wetting, or stretching) is applied to the substrate, the microcapsules burst and release the encapsulated fragrance. In a stretchable article, application of a stretching force bursts the capsules in the coating, while leaving relatively few, if any, unburst microcapsules in the coating. Thus, the stretchable article releases most of available fragrance upon the first stretching force, leaving an insignificant amount of fragrance for subsequent stretching forces.

As such, a need currently exists for an improved technique for providing fragrance releasing microcapsules in conjunction with an elastic material that allows the fragrance to be released upon subsequent stretching forces during prolonged use of the elastic material.

SUMMARY OF THE INVENTION

Generally, the present invention is directed to, in one embodiment, an elastic laminate configured to release a fragrance upon stretching. The elastic laminate includes a nonwoven web facing laminated to an elastic material (e.g., film, strands, an elastic web, or combinations thereof). Fragrance releasing microcapsules are distributed in the thickness in the Z-direction of the internal fibrous structure of the nonwoven web. At least about 25 wt. % of the fragrance releasing microcapsules present in the elastic laminate can be embedded within the internal fibrous structure of the nonwoven web facing, such as from about 40 wt. % to about 85 wt. % of the fragrance releasing microcapsules, or from about 50 wt. % to about 75 wt. % of the fragrance releasing microcapsules. A binder composition (e.g., an adhesive) can be utilized to secure the fragrance releasing microcapsules within the internal fibrous structure of the nonwoven web facing.

The fragrance releasing microcapsules can have an average diameter of between about 1 micrometer and about 50 micrometers. In one embodiment, the fragrance releasing microcapsules contain a fragrance oil. The fragrance oil can be encapsulated within a capsule shell to form the microcapsule.

In another embodiment, the present invention is directed to a method of embedding fragrance releasing microcapsules into an elastic laminate. According to the method, a binder composition is applied to a nonwoven web such that the binder composition enters the internal fibrous structure of the nonwoven web. The binder composition includes fragrance releasing microcapsules. Thereafter, the nonwoven web is laminated to an elastic material to form an elastic laminate configured to release fragrance upon stretching. The nonwoven web can be necked prior to laminating to the elastic material. Alternatively, the nonwoven can be stretched prior to application of the binder composition and prior to lamination to the elastic material.

In one embodiment, the binder composition has a viscosity of less than about 100 cP, as measured with a Brookfield viscometer, type DV-I or LV-IV, at 60 rpm and 20° C. Also, in one embodiment, the method can further include the step of pressing the nonwoven web in a nip to force the fragrance releasing microcapsules into the internal fibrous structure of the nonwoven web. The nip can be a low-pressure nip, such as exerting a pressure of less than about 25 psi on the nonwoven web.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

Definitions

Figure 1:
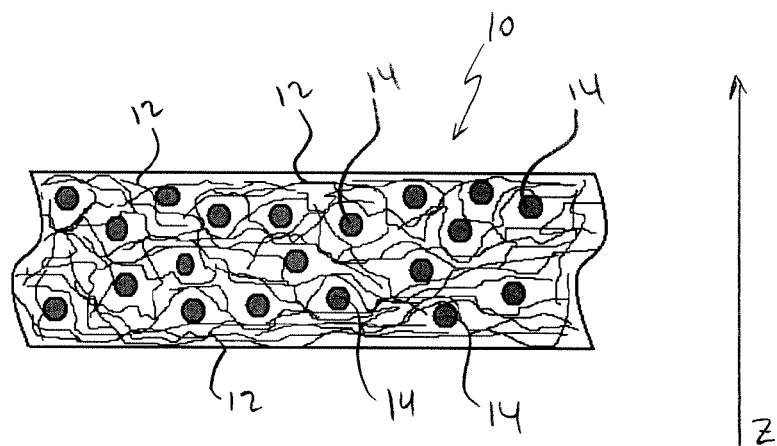
FIG. 1 illustrates a cross-sectional view of a nonwoven web having fragrance releasing microcapsules embedded throughout the Z-direction of the nonwoven web.

As used herein, the term "absorbent article" refers to any article capable of absorbing water or other fluids. Examples of some absorbent articles include, but are not limited to, personal care absorbent articles, such as diapers, training pants, absorbent underpants, fenestration materials, adult incontinence products, feminine hygiene products (e.g., sanitary napkins), and so forth; wound coverings; wipers; bed pads; shoe pads; clothing articles, such as perspiration pads, disposable swimming apparel, and so forth; air and water filtration devices; and so forth. Materials and processes suitable for forming such absorbent articles are well known to those skilled in the art.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblown fibers" refers to fibers formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin. et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonded fibers" refers to small diameter substantially continuous fibers that are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner. et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo. et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers can sometimes have diameters less than about 40 microns, and are often between about 5 to about 20 microns.

As used herein, the terms "machine direction" or "MD" generally refers to the direction in which a material is produced. The term "cross-machine direction" or "CD" refers to the direction perpendicular to the machine direction. Dimensions measured in the cross-machine direction are referred to as "width" dimension, while dimensions measured in the machine direction are referred to as "length" dimensions.

As used herein, the term "elastomeric" and "elastic" and refers to a material that, upon application of a stretching force, is stretchable in a direction (such as the MD or CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a 2.54-cm sample of a material that is stretchable to at least 3.81 centimeters and which, upon release of the stretching force, will recover to a length of not more than 3.175 centimeters. Desirably, the material contracts or recovers at least 50%, and even more desirably, at least 80% of the stretched length.

As used herein the terms "extensible" or "extensibility" generally refers to a material that stretches or extends in the direction of an applied force by at least about 50% of its relaxed length or width. An extensible material does not necessarily have recovery properties. For example, an elastomeric material is an extensible material having recovery properties. A meltblown web may be extensible, but not have recovery properties, and thus, be an extensible, non-elastic material.

As used herein, the term "percent stretch" refers to the degree to which a material stretches in a given direction when subjected to a certain force. In particular, percent stretch is determined by measuring the increase in length of the material in the stretched dimension, dividing that value by the original dimension of the material, and then multiplying by 100. Such measurements are determined using the "strip elongation test", which is substantially in accordance with the specifications of ASTM D5035-95. Specifically, the test uses two clamps, each having two jaws with each jaw having a facing in contact with the sample. The clamps hold the material in the same plane, usually vertically, separated by 3 inches (7.62 cm) and move apart at a specified rate of extension. The sample size is 3 inches by 6 inches (7.62 cm×15.24 cm), with a jaw facing height of 1 inch (2.54 cm) and width of 3 inches (7.62 cm), and a constant rate of extension of 300 mm/min. The specimen is clamped in, for example, a Sintech 2/S tester with a Renew MTS mongoose box (control) and using TESTWORKS 4.07b software (Sintech Corp, of Cary, N.C.). The test is conducted under ambient conditions. Results are generally reported as an average of three specimens and may be performed with the specimen in the cross direction (CD) and/or the machine direction (MD).

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations within the scope of the appended claims and their equivalents.

In general, the present invention is directed to an elastic laminate having fragrance releasing microcapsules configured to release the microencapsulated fragrance upon stretching the laminate. The elastic laminate can continue to release fresh fragrance even after the first stretching force is applied. Thus, the effective life of the elastic laminate can be extended.

The present inventors have discovered that embedding fragrance releasing microcapsules throughout the thickness (i.e., the Z-direction perpendicular to the MD and CD directions) of a nonwoven web facing of the elastic laminate provides multiple advantages over simply coating microcapsules on a surface of the web. The presence of fragrance releasing microcapsules positioned at varying depths of the nonwoven web can create a web capable of releasing fragrance even after a first stretching force is applied to the laminate. Additionally, the amount of fragrance released from the microcapsules in the nonwoven web facing can be controlled according to the strength of the stretching forces applied to the laminate.

No matter the application method, at least a portion of the fragrance releasing microcapsules is embedded within the internal fibrous structure of the web. In some embodiments, at least about 25 wt. % of the fragrance releasing microcapsules present in the web can be embedded within the Z-direction of the web, such as greater than about 35 wt. % of the fragrance releasing microcapsules. For example, from about 40 wt. % to about 85 wt. % of the fragrance releasing microcapsules present in the web can be embedded within the Z-direction of the web, such as from about 50 wt. % to about 75 wt. % of the fragrance releasing microcapsules. Referring to FIG. 1, a cross-section of an exemplary nonwoven web 10 of fibers 12 is shown having fragrance releasing microcapsules 14 randomly embedded throughout the Z-direction.

By embedding the fragrance releasing microcapsules throughout the internal fibrous structure of the web in the Z-direction, as opposed to applying the microcapsules in a coating on a surface of the web, the resulting laminate can provide freshly released fragrance during extended use of the laminate, even after several stretching forces have been applied to the web.

Figure 2:
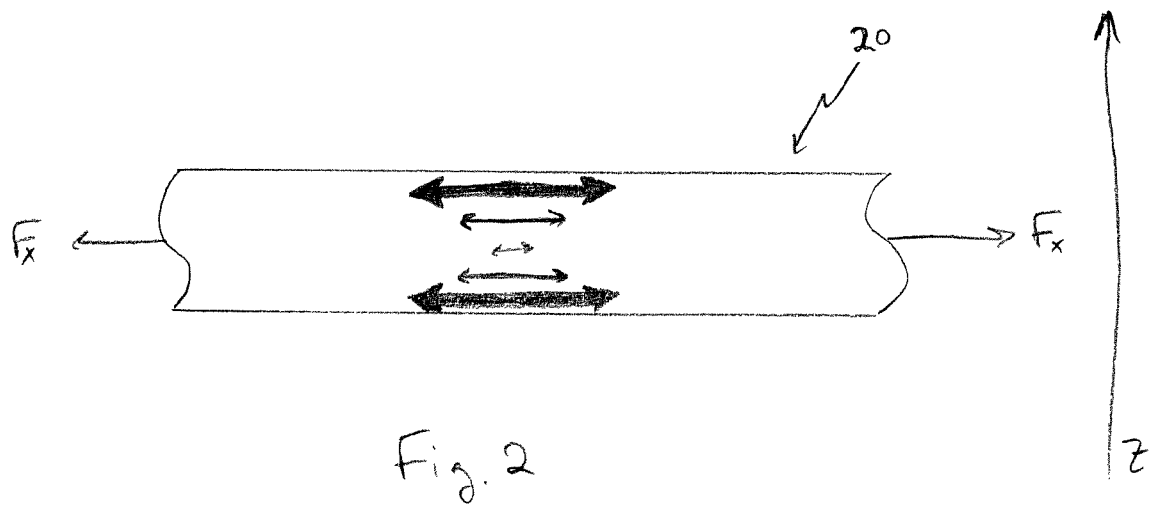
FIG. 2 illustrates the force gradient present in the Z-direction of the nonwoven web when a stretching force is applied in the plane of the web.

During stretching in the plane of the web (i.e., in the MD and/or CD direction), a force gradient in the Z-direction is formed within the web. This force gradient creates more strain in the fibers or fiber segments closest to the surfaces of the nonwoven web, while less strain in the fibers or fiber segments nearer the center of the web. Referring to FIG. 2, a cross-section of nonwoven web 20 is shown with a stretching force $F_x$ applied in the plane of the web. The force gradient is represented in the Z-direction, with the size of the arrows representing the relative amount of strain located throughout the Z-direction of the web.

The greater fiber strain along the surfaces of the nonwoven web can cause the fragrance releasing microcapsules positioned along the surface of the web to rupture at a lower biasing force than those microcapsules located within the center of the web in the Z-direction. Thus, when incorporated into an elastic laminate, the nonwoven web having fragrance releasing microcapsules throughout the Z-direction of the web can provide a laminate capable of releasing fragrance upon subsequent stretching forces.

In one embodiment, stretching the elastic laminate having a nonwoven layer with fragrance releasing microcapsules embedded throughout the Z-direction to a biased length of about 105% to about 115% can burst the microcapsules regions closest to the surface of the web, while a substantial portion of the microcapsules embedded in the web near the center of the web remain intact. For example, at least 25 wt. % of the microcapsules within the nonwoven web can remain intact and unburst after stretching to a biased length of about 115% or less. Thus, subsequent stretching of the web, such as to a biased length between about 125% to about 140%, can burst some of the remaining microcapsules creating a fresh burst of fragrance upon the subsequent stretching. Furthermore, stretching to a biased length of about 150% or greater can burst even more microcapsules creating another fresh burst of fragrance.

I. Fragrance Releasing Microcapsules

Generally speaking, any of a variety of fragrance releasing microcapsules may be utilized in the present invention. Typically, the fragrance releasing microcapsules have a fragrance composition (e.g., perfumes, fragrance oils, etc.) encapsulated within a capsule shell. Several fragrance releasing microcapsules are readily commercially available from various suppliers. For instance, particularly suitable microcapsules are available from Scentisphere LLC of Valhalla, N.Y.

The capsule shell is configured to encapsulate the fragrance and, upon stretching of the elastic laminate, rupture to create one or more openings in the microcapsule shell through which the fragrance can escape. The microcapsules useful in the present invention may comprise any rupturable capsule (typically polymeric) containing a liquid ingredient therein.

The shell of the microcapsules exhibits sufficient strength to withstand the processing conditions employed to embed the microcapsules into the nonwoven layer, as well as the lamination process to the elastic material. However, some microcapsules may rupture during the embedding process and/or the lamination process. In one embodiment, less than about 10% of the microcapsules can rupture during these processes.

The encapsulated fragrance can provide any desired aroma or scent, and is generally provided from material that is relatively volatile, so as to quickly release their aroma or scent upon rupture of the microcapsule. The material contained in the microcapsules can be any of a variety of liquids, including solutions, dispersions, and gelled materials. For example, certain organic solids or liquids (e.g., organic oils) that readily volatize upon exposure to air can be included in the fragrance composition. In one embodiment, the fragrance can be provided from a fragrance oil, such as those oils commercially available from Scentisphere LLC of Valhalla, N.Y.

Any suitable method for making the fragrance releasing microcapsules can be utilized. A common feature of many encapsulation processes is that they require the fragrance material to be encapsulated to be dispersed in aqueous solutions of polymers, pre-condensates, surfactants, and the like prior to formation of the capsule walls. Therefore, materials having low solubility in water, such as highly hydrophobic materials may ease the encapsulation process, as they will tend to remain in the dispersed perfume phase and partition only slightly into the aqueous solution. Other exemplary processes are described in U.S. Pat. Nos. 3,516,941; 4,409,156; 4,087,376; 4,493,869; 4,654,256; 4,808,408; 4,908,252; 5,043,161 and 5,180,637, 6,329,057, and 6,261,483, all of which are incorporated by reference as if set forth in their entirety.

The average diameter of the microcapsules is generally between about 1 micrometer and about 50 micrometers, such as from about 5 micrometers to about 30 micrometers.

II. Binder Compositions Having Fragrance Releasing Microcapsules

Typically, the fragrance releasing microcapsules are applied to the nonwoven web in a binder composition in order to embed the microcapsules within the internal fibrous structure of the nonwoven web. The binder composition acts not only as a carrier of the microcapsules during application to and saturation of the web, but also serves to secure the microcapsules within the internal fibrous structure of the web (e.g., bond or adhere the microcapsules to the fibers of the web).

The concentration of the fragrance releasing microcapsules in the binder composition may be varied to help control the concentration and add-on in the resulting nonwoven web. For example, the binder composition may have a solids content of from about 5% to about 90% by weight, in some embodiments from about 10% to about 80%, and in some embodiments, from about 20% to about 70%. By varying the solids content of the binder composition, the presence of the fragrance releasing microcapsules and other components in the binder composition may be controlled. Forming a binder composition with higher levels of microcapsules can increase the solids content so that a greater percentage of microcapsules is incorporated into the composition during the application process. If desired, thickeners or other viscosity modifiers may also be employed in the coating formulation to increase or decrease viscosity.

In one embodiment, the binder composition containing the fragrance releasing microcapsules has a viscosity low enough to allow saturation of the web with the binder composition. Thus, the binder composition can distribute the fragrance releasing microcapsules throughout the internal fibrous structure of the nonwoven web. Generally, the fragrance releasing microcapsules can be randomly distributed throughout the internal fibrous structure of the web. For example, the microcapsules can be substantially homogenously distributed in the Z-direction of the web. In this embodiment, the viscosity of the binder composition is low enough to allow the binder composition to saturate the internal fibrous structure of the web, and subsequently distribute the microcapsules throughout the Z-direction of the nonwoven web. In one embodiment, the viscosity of the binder composition can be less than about 100 centipoise (cP), such as from about 0 cP to about 75 cP, such as measured with a Brookfield viscometer, type DV-I or LV-IV, at 60 rpm and 20° C. For instance, the binder composition's viscosity can be less than about 50 centipoise (cP), such as from about 5 cP to about 30 cP.

In an alternative embodiment, where the binder composition has a higher viscosity, the binder composition containing the fragrance releasing microcapsules can be pressed or otherwise forced into the internal fibrous structure of the web. In this embodiment, the binder composition can have a higher viscosity, such as greater than about 100 cP. For example, in one embodiment, the binder composition can have a viscosity of from about 200 cP to about 10,000 cP, or from about 300 cP to about 1000 cP. However, due to the relatively high viscosity of the binder composition, the binder composition may stay on the surface of the web and may not appreciably saturate the internal fibrous structure of the web. As such, the microcapsules do not appreciably penetrate the Z-direction of the web. Thus, the binder composition can be pressed into the fibrous web, such that the fragrance releasing microcapsules become embedded within the internal fibrous structure of the web. However, the amount of pressure exerted onto the web should be sufficient to drive the binder composition and microcapsules into the internal fibrous structure of the web without rupturing a significant amount of the microcapsules. Thus, a low-pressure pressing process can be utilized.

In this embodiment, the nonwoven web having a binder composition and the fragrance releasing microcapsules can be passed through a low-pressure nip. The low pressure nip can be created from two calendering rolls, as know in the art. To be considered a low pressure nip, the peak pressure applied to the web during the pressing process is such that will not substantially densify the web nor prematurely burst a significant amount of the microcapsules (e.g., less than 10% of the microcapsules). Exemplary peak pressures may be any of the following: about 25 psi or less, about 20 psi or less, about 10 psi or less, about 5 psi or less, about 2 psi or less, about 1 psi or less, and about 0.8 psi or less, dependent on the strength of the microcapsules.

Accordingly, the binder composition containing the microcapsules can be applied to the nonwoven web by any manner. A variety of techniques may be used for applying the fragrance releasing microcapsules in the above-described manners. For example, the binder composition containing the microcapsules can be printed onto the web, saturated into the web, flood coated, and the like. Other suitable coating equipment and methods may also be described in U.S. Pat. No. 5,085,514 to Mallik, et al.; U.S. Pat. No. 5,922,406 to Ludford, III; and U.S. Pat. No. 6,299,729 to Heath, et al., which are incorporated herein in their entirety by reference thereto for all purposes.

In accordance with one embodiment, any of a variety of low pressure printing technologies may be utilized to print the binder composition onto the web so as to minimize premature rupturing of the microcapsules. Low pressure printing technologies are generally considered to be those in which the peak pressure applied to the web during the printing process is such that will not substantially densify the web. Exemplary peak pressures may be any of the following: about 25 psi or less, about 10 psi or less, about 5 psi or less, about 2 psi or less, about 1 psi or less, and about 0.8 psi or less. The same ranges may be applied to the mean pressure on the web during contact with a printing device. The binder composition may be applied directly to a surface of the nonwoven web using rotogravure or gravure printing, either direct or indirect (off-set). Suitable gravure printing techniques are also described in U.S. Pat. No. 6,231,719 to Garvey, et al., which is incorporated herein in its entirety by reference thereto for all purposes. Moreover, besides gravure printing, it should be understood that other printing techniques, such as flexographic printing, may also be used to apply the coating.

In addition to the printing techniques mentioned above, any other suitable application technique may be used in the present invention. For example, the binder composition may be sprayed onto the nonwoven web. Any equipment suitable for spraying an additive onto a web may be utilized in the present invention. One example of suitable spraying equipment includes external mix, air atomizing nozzles, such as the 2 mm nozzle available from V.I.B. Systems, Inc., Tucker, Ga. Another nozzle that can be used is an H ⅛" VV-SS 650017 VeeJet spray nozzle available from Spraying Systems, Inc. of Milwaukee, Wis. Still other spraying techniques and equipment are described in U.S. Pat. No. 5,164,046 to Ampulski, et al., which is incorporated herein in its entirety by reference thereto for all purposes. Likewise, a brush spray application technique may also be employed, such as described in U.S. Pat. No. 5,628,788 to Garavaglia, et al., which is incorporated herein in its entirety by reference thereto for all purposes.

Besides the above-mentioned techniques, the binder composition may also be applied as a foam composition. Several suitable techniques for forming a foam composition and applying the composition to a dry web are described in U.S. Pat. No. 6,607,783 to Vander Heiden, et al. and U.S. Pat. No. 6,797,116 to Capizzi, which are incorporated herein in their entirety by reference thereto for all purposes. Still other suitable coating techniques may include, for instance, bar, roll, knife, curtain, slot-die, dip-coating, drop-coating, extrusion, etc.

In one embodiment, the binder composition containing the microcapsules can be uniformly applied to the web. However, to further enhance extensibility, absorbency, and/or some other characteristic of the web, it is sometimes desired to apply the binder composition to less than 100% of the area of the web, in some embodiments from about 10% to about 80%, and in some embodiments, from about 20% to about 60% of the area of the web. In one particular embodiment, the binder composition containing the microcapsules can be applied to the web in a preselected pattern (e.g., reticular pattern, diamond-shaped grid, dots, and so forth). Although not required, such a patterned coating may provide sufficient fragrance releasing ability without saturating a substantial portion of the area of the web. This may be desired to optimize flexibility, absorbency, or other characteristics of the web.

Regardless of the method of application, the binder composition may sometimes be dried at a certain temperature to drive the solvent from the composition. For example, the web may be heated to a temperature of at least about 50° C., in some embodiments at least about 70° C., and in some embodiments, at least about 80° C. It should be understood, however, that relatively small amounts of solvent may still be present. For example, the dried binder composition may contain a solvent in an amount less than about 10% by weight, in some embodiments less than about 5% by weight, and in some embodiments, less than about 1% by weight.

The binder composition can include an adhesion promoter (e.g., an adhesive), glue, or any other binder that is configured to adhere the fragrance releasing microcapsules to the fibers of the web. Any suitable adhesive may be included in the binder composition. In one particular embodiment, the binder composition can be a drying adhesive, such as rubber cement. Rubber cement is an adhesive made from polymers (typically latex) mixed in a solvent (e.g., acetone, hexane, heptane or benzene) to keep them fluid enough to be used. A small percentage of alcohol can be added to the mix, if desired. As the solvents quickly evaporate after application to the web, the "rubber" portion (i.e. polymers) remains behind, forming a strong yet flexible bond.

Rubber cement compositions are particularly suited for application of the fragrance releasing microcapsules since the solvent system does not have an appreciable amount of water present. In many microcapsules, the presence of water can solubilize the microcapsule shell, which is often formed from hydrophilic or a water-soluble polymer.

In an alternative embodiment, the binder composition can be a hot-melt adhesive. When using a hot melt adhesive as a binder composition, the fragrance releasing microcapsules are selected to withstand the heating and melting of the binder composition during application to the web. Exemplary hot melt adhesives are described in U.S. Pat. No. 6,774,069, which is incorporated by reference herein, and may be desired since these adhesives can be applied at a relatively low temperature.

Additionally, other adhesion promoters can be utilized within the binder composition. For example, Carboset 514H, available commercially from Noveon, Inc. of Cleveland, Ohio, is an acrylic colloidal dispersion polymer supplied in ammonia water, which can dry to a clear, water-resistant, non-tacky thermoplastic film.

Besides having various functional benefits, the web may also have aesthetic benefits as well. In one embodiment, the binder composition can contain a coloring agent, such as a pigment or dye. For example, the binder composition can be an ink composition that contains a binder. Various pigments and/or dyes may be employed to alter the color of the binder composition. Likewise, the pigments, dyes, or other masking agents may be applied to the web separately from the binder composition.

When dried, the relative percentages and solids add-on level of the resulting web having microcapsules distributed throughout the internal fibrous structure may vary to achieve the desired level of fragrance release upon stretching. The "solids add-on level" is determined by subtracting the weight of the untreated web from the weight of the treated web (after drying), dividing this calculated weight by the weight of the untreated web, and then multiplying by 100%. One particular benefit of the present invention is that high solids add-on levels and fragrance releasing ability are achievable without a substantial sacrifice in durability of the web and resulting elastic laminate. In some embodiments, the add-on level of the binder composition, including the microcapsules, is at least about 2%, in some embodiments from about 4% to about 20%, and in some embodiments, from about 6% to about 15%. Further, the dried binder composition may contain from about 10 wt. % to about 80 wt. %, in some embodiments from about 20 wt. % from about 70 wt. %, and in some embodiments, from about 40 wt. % to about 60 wt. % of the fragrance releasing microcapsules. Likewise, the dried binder composition may also contain from about 10 wt. % to about 80 wt. %, in some embodiments from about 10 wt. % from about 60 wt. %, and in some embodiments, from about 30 wt. % to about 50 wt. % of binder.

III. Nonwoven Web Facings

The nonwoven web facing can be any suitable web for use in an elastic laminate. In most embodiments, the nonwoven web is constructed from polymeric fibers, such as synthetic fibers. Exemplary polymers for use in forming nonwoven web may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. If desired, biodegradable polymers, such as those described above, may also be employed. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. It should be noted that the polymer(s) may also contain other additives, such as processing aids or treatment compositions to impart desired properties to the fibers, residual amounts of solvents, pigments or colorants, and so forth.

Monocomponent and/or multicomponent fibers may be used to form the nonwoven web facing. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack. et al., U.S. Pat. No. 5,108,820 to Kaneko, et al., U.S. Pat. No. 4,795,668 to Kruege. et al., U.S. Pat. No. 5,382,400 to Pike, et al., U.S. Pat. No. 5,336,552 to Strack. et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,277,976 to Hogle. et al., U.S. Pat. No. 5,162,074 to Hills U.S. Pat. No. 5,466,410 to Hills, U.S. Pat. No. 5,069,970 to Largman. et al., and U.S. Pat. No. 5,057,368 to Largman. et al., which are incorporated herein in their entirety by reference thereto for all purposes.

Although any combination of polymers may be used, the polymers of the multicomponent fibers are typically made from thermoplastic materials with different glass transition or melting temperatures where a first component (e.g., sheath) melts at a temperature lower than a second component (e.g., core). Softening or melting of the first polymer component of the multicomponent fiber allows the multicomponent fibers to form a tacky skeletal structure, which upon cooling, stabilizes the fibrous structure. For example, the multicomponent fibers may have from about 5% to about 80%, and in some embodiments, from about 10% to about 60% by weight of the low melting polymer. Further, the multicomponent fibers may have from about 95% to about 20%, and in some embodiments, from about 90% to about 40%, by weight of the high melting polymer. Some examples of known sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del.

Fibers of any desired length may be employed, such as staple fibers, continuous fibers, etc. In one particular embodiment, for example, staple fibers may be used that have a fiber length in the range of from about 1 to about 150 millimeters, in some embodiments from about 5 to about 50 millimeters, in some embodiments from about 10 to about 40 millimeters, and in some embodiments, from about 10 to about 25 millimeters. Although not required, carding techniques may be employed to form fibrous layers with staple fibers as is well known in the art. For example, fibers may be formed into a carded web by placing bales of the fibers into a picker that separates the fibers. Next, the fibers are sent through a combing or carding unit that further breaks apart and aligns the fibers in the machine direction so as to form a machine direction-oriented fibrous nonwoven web. The carded web may then be bonded using known techniques to form a bonded carded nonwoven web.

If desired, the nonwoven web used to form the nonwoven layer of the elastic laminate may have a multi-layer structure. When multiple layers of nonwoven webs are present, any of the nonwoven webs include the microcapsules throughout its thickness. For example, one or all of the nonwoven webs in the nonwoven layer can include fragrance releasing microcapsules distributed throughout the Z-direction of the web. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., which are incorporated herein in their entirety by reference thereto for all purposes. In addition, commercially available SMS laminates may be obtained from Kimberly-Clark Corporation under the designations Spunguard® and Evolution®.

Another example of a multi-layered structure is a spunbond web produced on a multiple spin bank machine in which a spin bank deposits fibers over a layer of fibers deposited from a previous spin bank. Such an individual spunbond nonwoven web may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven web may be provided as two or more individually produced layers of a spunbond web, a carded web, etc., which have been bonded together to form the nonwoven web. These individually produced layers may differ in terms of production method, basis weight, composition, and fibers as discussed above.

The nonwoven web may also contain an additional fibrous component such that it is considered a composite. For example, a nonwoven web may be entangled with another fibrous component using any of a variety of entanglement techniques known in the art (e.g., hydraulic, air, mechanical, etc.). In one embodiment, the nonwoven web is integrally entangled with cellulosic fibers using hydraulic entanglement. Hydraulically entangled nonwoven webs of staple length and continuous fibers are disclosed, for example, in U.S. Pat. No. 3,494,821 to Evans and U.S. Pat. No. 4,144,370 to Boulton, which are incorporated herein in their entirety by reference thereto for all purposes. Hydraulically entangled composite nonwoven webs of a continuous fiber nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes.

IV. Elastic Laminates

Various elastic laminates may be incorporated with fragrance releasing microcapsules in accordance with the present invention, provided that the elastic laminate has at least one nonwoven web facing laminated to an elastic material. Regardless of the material selected, the laminate is "stretchable", i.e., upon application of a force, the laminate may be stretched to a biased length that is at least about 125%, and in some embodiments, at least about 150% its unstretched length. Additionally, the elastic laminate will also recover at least about 50% of its elongation upon release of the stretching, biasing force.

Generally speaking, the nonwoven web facing may be laminated to the elastic material to reduce the coefficient of friction and enhance the cloth-like feel of its surface. The basis weight of the nonwoven web facing may generally vary, such as from about 5 grams per square meter ("gsm") to 120 gsm, in some embodiments from about 8 gsm to about 70 gsm, and in some embodiments, from about 10 gsm to about 35 gsm.

The elastic material may be a film, foam, strands, elastic nonwoven web, and so forth. In one embodiment, the elastic material includes a film. Any known technique may be used to form a film, including blowing, casting, flat die extruding, etc. In one particular embodiment, the film may be formed by a blown process in which a gas (e.g., air) is used to expand a bubble of a melt extruded polymer through an annular die. The bubble is then collapsed and collected in flat film form. Processes for producing blown films are described, for instance, in U.S. Pat. No. 3,354,506 to Ralev; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes. Although not required, the film may be stretched to improve its properties. For example, the film may be drawn by rolls rotating at different speeds of rotation so that the sheet is stretched to the desired draw ratio in the longitudinal direction (machine direction). In addition, the uniaxially stretched film may also be oriented in the cross-machine direction to form a "biaxially stretched" film. For example, the film may be clamped at its lateral edges by chain clips and conveyed into a tenter oven. In the tenter oven, the film may be drawn in the cross-machine direction to the desired draw ratio by chain clips diverged in their forward travel. Various parameters of a stretching operation may be selectively controlled, including the draw ratio, stretching temperature, and so forth. In some embodiments, for example, the film is stretched in the machine direction at a stretch ratio of from about 1.5 to about 7.0, in some embodiments from about 1.8 to about 5.0, and in some embodiments, from about 2.0 to about 4.5. The stretch ratio may be determined by dividing the length of the stretched film by its length before stretching. The stretch ratio may also be approximately the same as the draw ratio, which may be determined by dividing the linear speed of the film upon stretching (e.g., speed of the nip rolls) by the linear speed at which the film is formed (e.g., speed of casting rolls or blown nip rolls). The film may be stretched at a temperature from about 15° C. to about 50° C., in some embodiments from about 25° C. to about 40° C., and in some embodiments, from about 30° C. to about 40° C. Preferably, the film is "cold drawn", i.e., stretched without the application of external heat (e.g., heated rolls).

The film may be a mono- or multi-layered film. Multilayer films may be prepared by co-extrusion of the layers, extrusion coating, or by any conventional layering process. Such multilayer films normally contain a base layer and skin layer, but may contain any number of layers desired. For example, the multilayer film may be formed from a base layer and one or more skin layers, wherein the base layer is formed from a block copolymer in accordance with the present invention. In such embodiments, the skin layer(s) may be formed from any film-forming polymer. If desired, the skin layer(s) may contain a softer, lower melting polymer or polymer blend that renders the layer(s) more suitable as heat seal bonding layers for thermally bonding the film to a nonwoven web facing. In most embodiments, the skin layer(s) are formed from an olefin polymer. Additional film-forming polymers that may be suitable for use with the present invention, alone or in combination with other polymers, include ethylene vinyl acetate, ethylene ethyl acrylate, ethylene acrylic acid, ethylene methyl acrylate, ethylene normal butyl acrylate, nylon, ethylene vinyl alcohol, polystyrene, polyurethane, and so forth.

In another embodiment of the present invention, the elastic material includes a plurality of strands. The number of strands may vary as desired, such as from 5 to about 20, in some embodiments from about 7 to about 18, and in some embodiments, from about 8 to 15 strands per cross-directional inch. The strands may have a circular cross-section, but may alternatively have other cross-sectional geometries such as elliptical, rectangular as in ribbon-like strands, triangular, multilobal, etc. The diameter of the strands (the widest cross-sectional dimension) may vary as desired, such as within a range of from 0.1 to about 4 millimeters, in some embodiments from about 0.2 to about 2.5 millimeters, and in some embodiments, from 0.5 to about 2 millimeters. Further, the strands may generally be arranged in any direction or pattern. For example, in one embodiment, the strands are arranged in a direction that is substantially parallel to the machine direction and are desirably spaced apart from each other across the cross machine direction at similar intervals. The strands may be substantially continuous in length so that they are in the form of filaments. Such filaments may be produced using any of a variety of known techniques, such as by melt extruding a polymer from a die having a series of extrusion capillaries arranged in a row. As is well known in the art, meltblown dies may be suitable for forming the filaments, except that the high velocity gas streams used in fiber attenuation are generally not employed. Rather, the molten polymer extrudate is pumped from the die capillaries and allowed to extend away from the die under the impetus of gravity.

If desired, a layer of the aforementioned strands may also be laminated to an additional layer (e.g., meltblown web) to help secure the strands to the nonwoven web facing so that they are less likely to loosen during use. Examples of such laminates are described in more detail, for instance, in U.S. Pat. No. 5,385,775 to Wright and U.S. Patent Application Publication No. 2005/0170729 to Stadelman. et al., which are incorporated herein in their entirety by reference thereto for all purposes. In one embodiment, the strands contain the block copolymer of the present invention and the meltblown web contains a polyolefin.

In one embodiment, a thermoplastic elastomer may be employed to improve the elastic performance of the resulting elastic laminate. Any of a variety of thermoplastic elastomers may generally be employed, such as elastomeric polyesters, elastomeric polyurethanes, elastomeric polyamides, elastomeric copolymers, and so forth. For example, the thermoplastic elastomer may be a block copolymer having blocks of a monoalkenyl arene polymer separated by a block of a conjugated diene polymer. Such block copolymers generally have a relatively high viscosity and are elastic in nature. Particularly suitable thermoplastic elastomers are available from Kraton Polymers LLC of Houston, Texas under the trade name KRATON®. KRATON® polymers include styrene-diene block copolymers, such as styrene-butadiene, styrene-isoprene, styrene-butadiene-styrene, and styrene-isoprene-styrene. KRATON® polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. Specific KRATON® block copolymers include those sold under the brand names G 1652, G 1657, G 1730, MD6673, and MD6973. Various suitable styrenic block copolymers are described in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers, LP of Houston, Tex. under the trade designation VECTOR™. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Other exemplary thermoplastic elastomers that may be used include polyurethane elastomeric materials such as, for example, those available under the trademark ESTANE from Noveon, polyamide elastomeric materials such as, for example, those available under the trademark PEBAX (polyether amide) from Atofina Chemicals Inc., of Philadelphia, Pa., and polyester elastomeric materials such as, for example, those available under the trade designation HYTREL from E.I. DuPont De Nemours & Company.

Furthermore, the elastic material may also contain a polyolefin, such as polyethylene, polypropylene, blends and copolymers thereof. In one particular embodiment, a polyethylene is employed that is a copolymer of ethylene or propylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene or propylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

The density of a linear olefin copolymer is a function of both the length and amount of the α-olefin. That is, the greater the length of the α-olefin and the greater the amount of α-olefin present, the lower the density of the copolymer. Although not necessarily required, linear "plastomers" are particularly desirable in that the content of α-olefin short chain branching content is such that the copolymer exhibits both plastic and elastomeric characteristics—i.e., a "plastomer." Because polymerization with α-olefin comonomers decreases crystallinity and density, the resulting plastomer normally has a density lower than that of thermoplastic polymers (e.g., LLDPE), but approaching and/or overlapping that of an elastomer. For example, the density of the plastomer may be about 0.91 grams per cubic centimeter (g/cm$^3$) or less, in some embodiments from about 0.85 to about 0.89 g/cm$^3$, and in some embodiments, from about 0.85 g/cm$^3$ to about 0.88 g/cm$^3$. Despite having a density similar to elastomers, plastomers generally exhibit a higher degree of crystallinity, are relatively non-tacky, and may be formed into pellets that are non-adhesive and relatively free flowing.

Any of a variety of known techniques may generally be employed to form such polyolefins. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al., which are incorporated herein in their entirety by reference thereto for all purposes.

Particularly suitable plastomers for use in the present invention may include ethylene-based copolymer plastomers available under the EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai, et al.; and U.S. Pat. No. 5,278,272 to Lai, et al., which are incorporated herein in their entirety by reference thereto for all purposes. Suitable propylene-based plastomers are likewise commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta. et al.; U.S. Pat. No. 5,539,056 to Yang, et al.; and U.S. Pat. No. 5,596,052 to Resconi, et al., which are incorporated herein in their entirety by reference thereto for all purposes.

Besides polymers, the elastic material of the present invention may also contain other components as is known in the art. In one embodiment, for example, the film contains a filler. Fillers are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. Nos. 5,997,981; 6,015,764; and 6,111,163 to McCormack, et al.; U.S. Pat. No. 5,932,497 to Morman. et al.; U.S. Pat. No. 6,461,457 to Taylor, et al., which are incorporated herein in their entirety by reference thereto for all purposes.

The fillers may have a spherical or non-spherical shape with average particle sizes in the range of from about 0.1 to about 7 microns. Examples of suitable fillers include, but are not limited to, calcium carbonate, various kinds of clay, silica, alumina, barium carbonate, sodium carbonate, magnesium carbonate, talc, barium sulfate, magnesium sulfate, aluminum sulfate, titanium dioxide, zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as stearic acid, may also be applied to the filler particles if desired. When utilized, the filler content may vary, such as from about 25 wt. % to about 75 wt. %, in some embodiments, from about 30 wt. % to about 70 wt. %, and in some embodiments, from about 40 wt. % to about 60 wt. % of the film.

Other additives may also be incorporated into the elastic material, such as crosslinking catalysts, pro-rad additives, melt stabilizers, processing stabilizers, heat stabilizers, light stabilizers, antioxidants, heat aging stabilizers, whitening agents, antiblocking agents, bonding agents, tackifiers, viscosity modifiers, etc. Suitable crosslinking catalysts, for instance, may include organic bases, carboxylic acids, and organometallic compounds, such as organic titanates and complexes or carboxylates of lead, cobalt, iron, nickel, zinc and tin (e.g., dibutyltindilaurate, dioctyltinmaleate, dibutyltindiacetate, dibutyltindioctoate, stannous acetate, stannous octoate, lead naphthenate, zinc caprylate, cobalt naphthenate; etc.). Suitable pro-rad additives may likewise include azo compounds, organic peroxides and polyfunctional vinyl or allyl compounds such as, triallyl cyanurate, triallyl isocyanurate, pentaerthritol tetramethacrylate, glutaraldehyde, polyester acrylate oligomers (e.g., available from Sartomer under the designation CN2303), ethylene glycol dimethacrylate, diallvl maleate, dipropargyl maleate, dipropargyl monoallyl cyanurate, dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2,5-di(t-butyl peroxy)hexane, lauryl peroxide, tert-butyl peracetate, azobisisobutyl nitrite, etc.

Examples of suitable tackifiers may include, for instance, hydrogenated hydrocarbon resins. REGALREZ™ hydrocarbon resins are examples of such hydrogenated hydrocarbon resins, and are available from Eastman Chemical. Other tackifiers are available from ExxonMobil under the ESCOREZ™ designation. Viscosity modifiers may also be employed, such as polyethylene wax (e.g., EPOLENE™ C-10 from Eastman Chemical). Phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant in the production of films. Some suitable hindered phenols include those available from Ciba Specialty Chemicals of under the trade name "Irganox®", such as Irganox® 1076, 1010, or E 201. Moreover, bonding agents may also be added to the film to facilitate bonding to additional materials (e.g., nonwoven web). When employed, such additives (e.g., tackifier, antioxidant, stabilizer, crosslinking agents, pro-rad additives, etc.) may each be present in an amount from about 0.001 wt. % to about 25 wt. %, in some embodiments, from about 0.005 wt. % to about 20 wt. %, and in some embodiments, from 0.01 wt. % to about 15 wt. % of the elastic material.

Any of a variety of techniques may be employed to laminate the nonwoven web facing and the elastic material together, including adhesive bonding; thermal bonding; ultrasonic bonding; microwave bonding; extrusion coating; and so forth. However, since the nonwoven web facing includes the fragrance releasing microcapsules prior to lamination, in most embodiments, the process is selected to minimize premature bursting of the microcapsules during lamination.

In one particular embodiment, adhesives may be employed to adhere the nonwoven web facing to the elastic material. Suitable adhesives include Rextac 2730 and 2723 available from Huntsman Polymers of Houston, Tex., as well as adhesives available from Bostik Findley, Inc, of Wauwatosa, Wis. The type and basis weight of the adhesive used will be determined on the elastic attributes desired in the final composite and end use. For instance, the basis weight of the adhesive may be from about 1.0 to about 3.0 gsm. The adhesive may be applied to the nonwoven web facings and/or the elastic material prior to lamination using any known technique, such as slot or melt spray adhesive systems. During lamination, the elastic material may in a stretched or relaxed condition depending on the desired properties of the resulting composite.

In this embodiment, the adhesive may also be the binder composition used to apply the fragrance releasing microcapsules to the internal fibrous structure of the web facing. As such, the adhesive can sufficiently saturate the web to distribute the fragrance releasing microcapsules throughout the Z-direction of the web, while a sufficient amount of adhesive remains on the surface of the web to adhere the elastic material.

Figure 3:
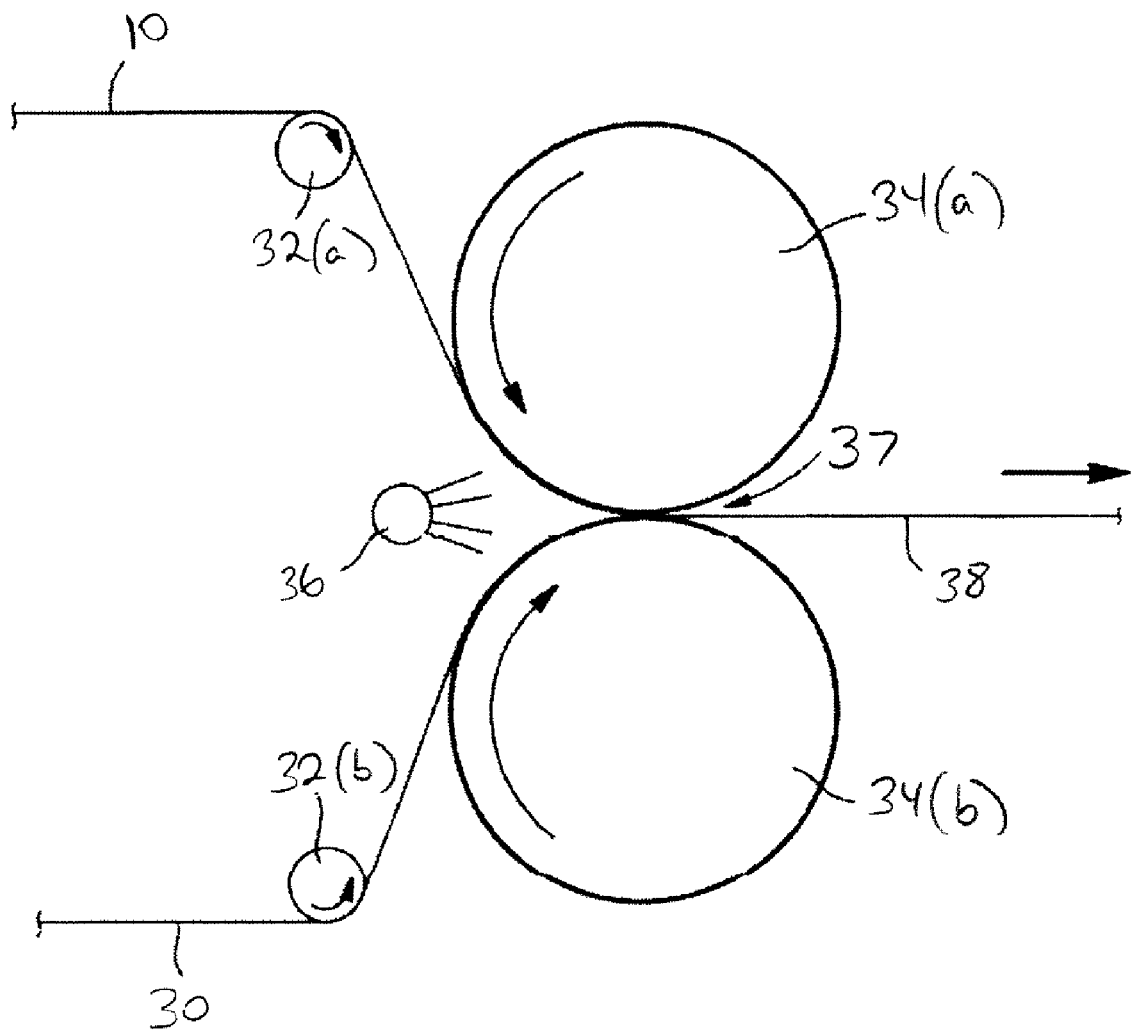
FIG. 3 illustrates an exemplary low-pressure nip for forming an elastic laminate according to one embodiment of the present invention.

In one embodiment, the nonwoven web facing and the elastic material can be combined together to form the elastic laminate in a low pressure nip that avoids rupturing a significant percentage of the microcapsules embedded in the web, such as less than 10 wt. %. For instance, the nip can exert about 25 psi or less on the nonwoven web and elastic material, such as about 20 psi or less, about 10 psi or less, about 5 psi or less, about 2 psi or less, about 1 psi or less, and about 0.8 psi or less, dependent on the strength of the microcapsules. For example, referring to FIG. 3, nonwoven web facing 10 containing microcapsules distributed throughout its thickness in the Z-direction is combined with elastic material 30 to form the elastic laminate 38. Nonwoven web facing 10 follows guide roll 32(a) into nip 37 formed by nip rolls 34(a) and 34(b). Likewise, elastic material 30 follows guide roll 32(b) into nip 37. Within the nip, the nonwoven web facing 10 is combined with elastic material 30 to form the elastic laminate 38. As shown, adhesive sprayer 36 applies an adhesive to join the nonwoven web facing 10 and the elastic material 30.

The nonwoven web facing may be necked in one or more directions prior to lamination to the film of the present invention. Suitable necking techniques are described in U.S. Pat. Nos. 5,336,545, 5,226,992, 4,981,747 and 4,965,122 to Morman, as well as U.S. Patent Application Publication No. 2004/0121687 to Morman. et al. Alternatively, the nonwoven web may remain relatively inextensible in a direction prior to lamination to the film.

In one embodiment, a separate coating containing fragrance releasing microcapsules can be applied to the surface of the nonwoven web facing. The fragrance releasing microcapsules in the coating composition can be the same or a different scent as those imbedded within the internal fibrous structure of the web facing. These fragrance releasing microcapsules in the coating can be configured to burst upon a relatively low stretching force (e.g., stretching to a biased length of about 105%). Thus, upon initial stretching, the fragrance releasing microcapsules of the coating can burst, while leaving the imbedded fragrance releasing microcapsules available to burst upon subsequent stretching forces applied to the laminate.

IV. Absorbent Articles

In general, the elastic laminate of the present invention may be utilized in a wide variety of applications in which releasing a desired fragrance upon stretching is desired, but is particularly useful as a component of an absorbent article. For example, the elastic laminate may be incorporated into an absorbent article, such as personal care absorbent articles (e.g., diapers, training pants, incontinence devices) and feminine hygiene products (e.g., sanitary napkins), where it can release a fragrance upon stretching.

The absorbent article normally includes a substantially liquid-impermeable layer (e.g., outer cover), a liquid-permeable layer (e.g., bodyside liner, surge layer, etc.), an absorbent core, and various other optional components. As is well known in the art, a variety of absorbent article components may possess elastic characteristics, such as waistbands, leg/cuff gasketing, ears, side panels, outer covers, and so forth. The crosslinked elastic material of the present invention may be employed for use in any of such components. In particular, the elastic laminate may be incorporated into regions of the absorbent article that are likely to be subjected to repeated stretching forces during use.

Figure 4:
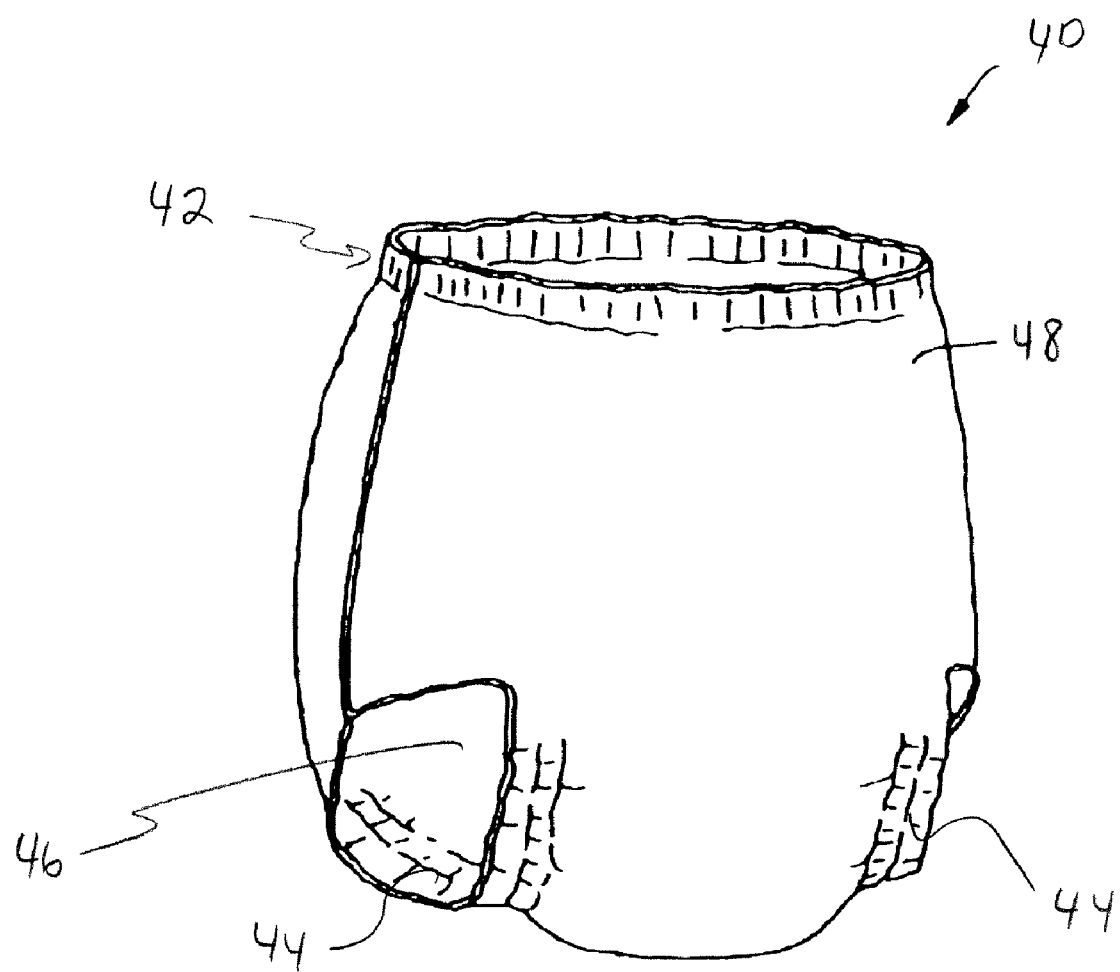
FIG. 4 illustrates a perspective view of an absorbent article that may be formed according to one embodiment of the present invention.
Figure 5:
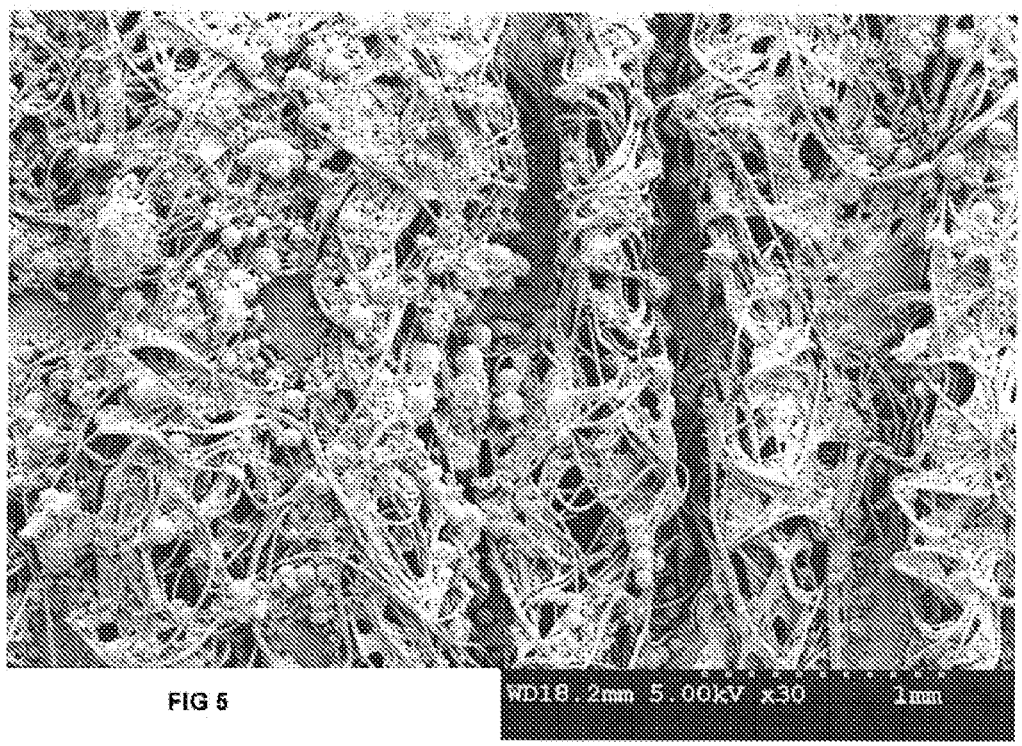
FIGS. 5-10 are pictures of a nonwoven web having fragrance releasing microcapsules embedded throughout the Z-direction of the nonwoven web.
Figure 6:
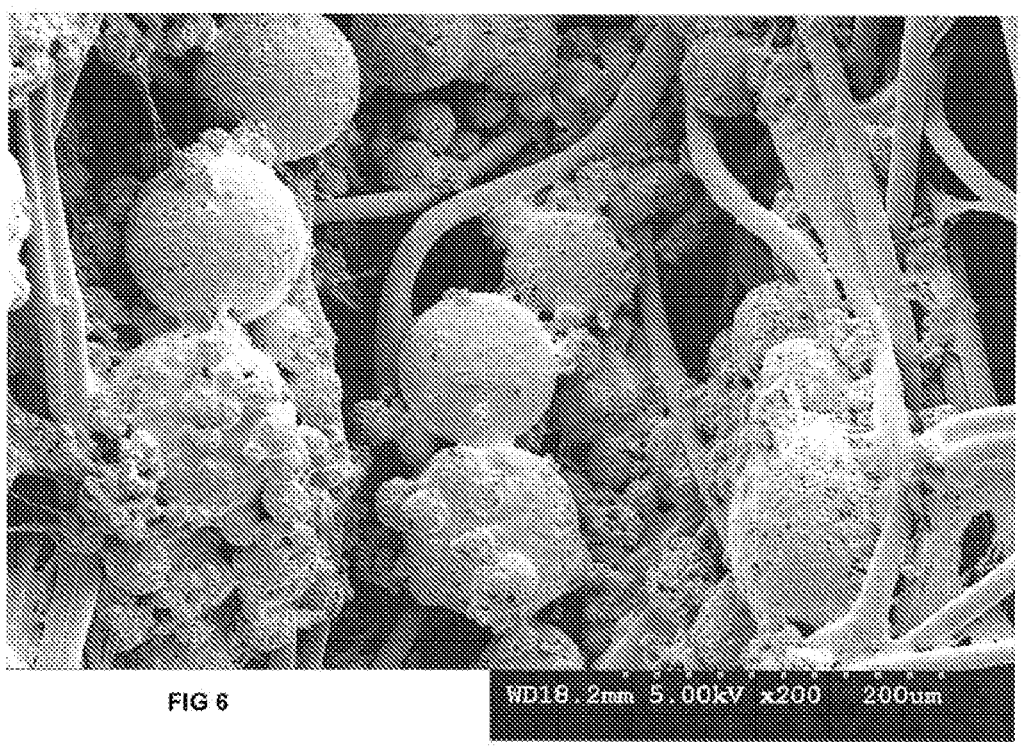
Figure 7:
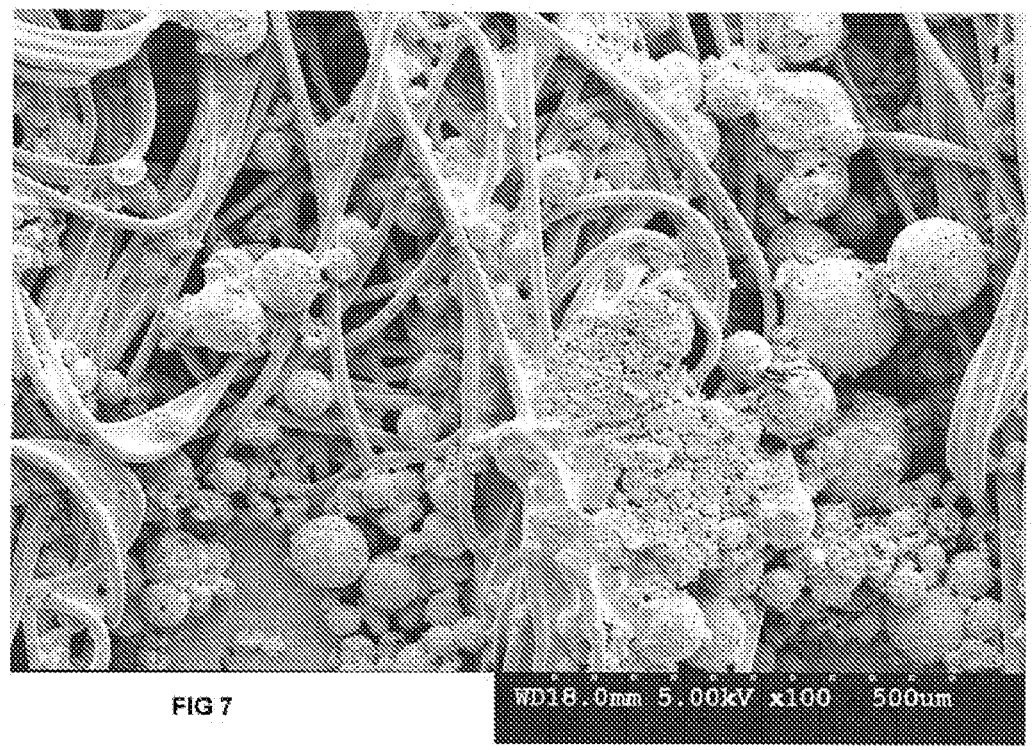
Figure 8:
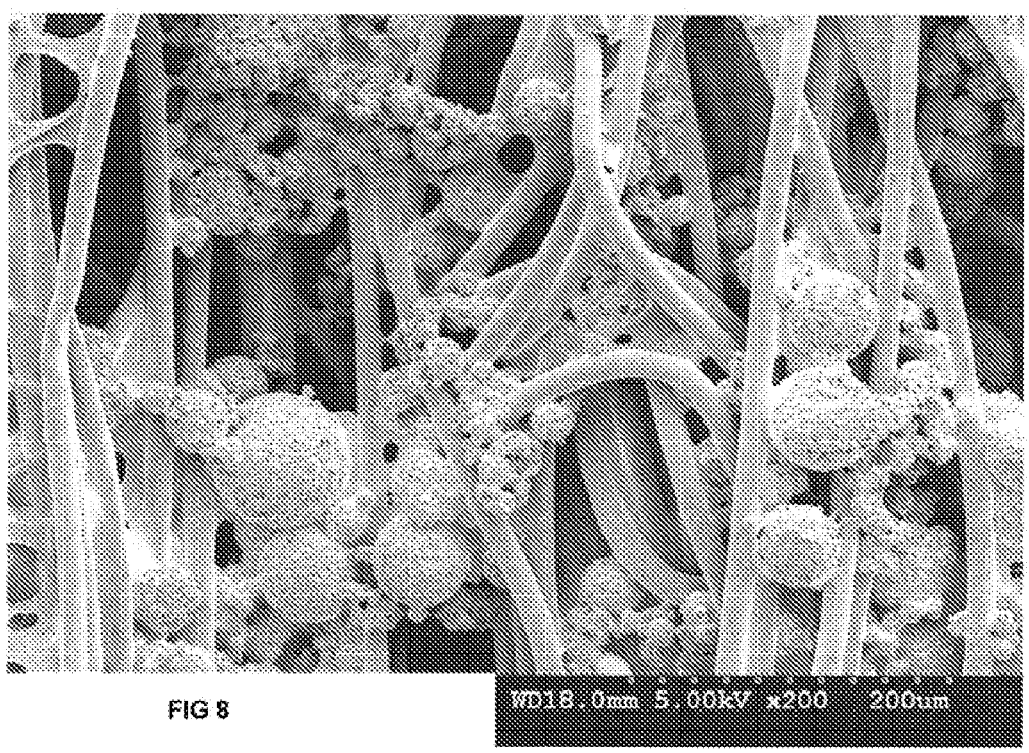
Figure 9:
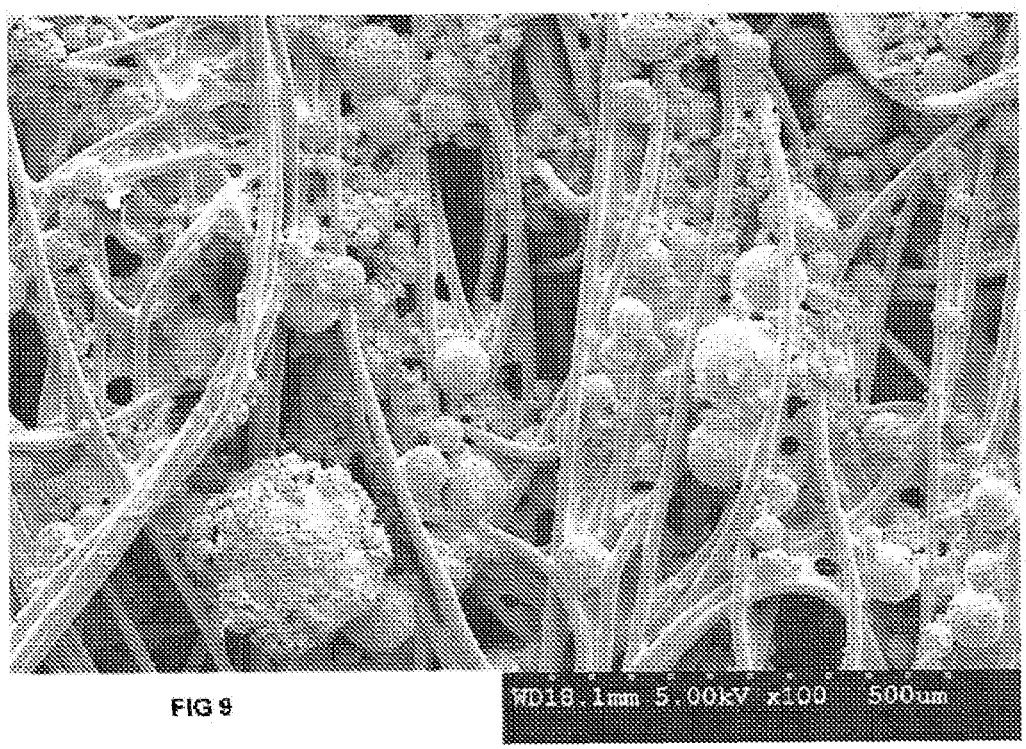
Figure 10:
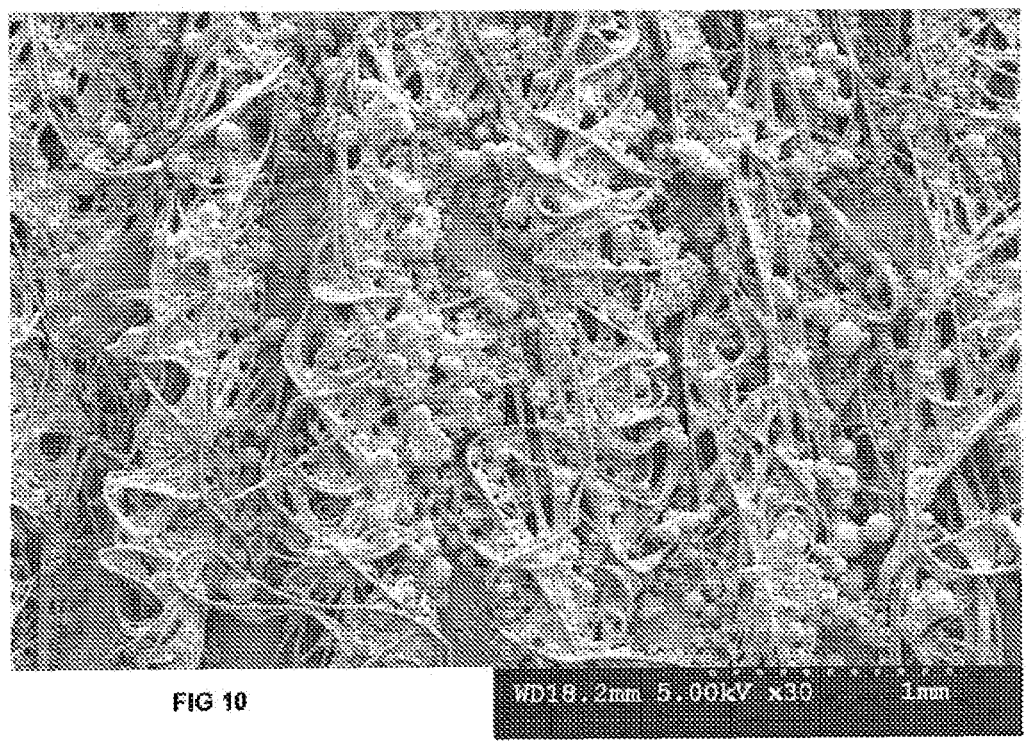

Referring to the exemplary training pant 40 depicted in FIG. 4, the waistband region 42 and leg cuff regions 44 can include the elastic laminate of the present invention. The training pant has an absorbent core (not shown) positioned between a liquid permeable topsheet 46 and a liquid impermeable backsheet 48.

Incorporation of the fragrance releasing microcapsules into a training pant can provide positive reinforcement during training, through the release of pleasant fragrance, whenever the wearer pulls down the training pant to use the bathroom facilities. Additionally, due to the distribution of the fragrance releasing microcapsules throughout the Z-direction of the web, fragrance can be released after several donnings of the training pant. Thus, the wearer can continually be reinforced during the training process.

Although various configurations of a training pant have been described above, it should be understood that other training pants and absorbent article configurations are also included within the scope of the present invention. In addition, the present invention is by no means limited to training pants. In fact, any other absorbent article may be formed in accordance with the present invention, including, but not limited to, other personal care absorbent articles, such as diapers, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Examples of diaper configurations suitable for use in connection with the elastic materials of the present invention that may include other components suitable for use on diapers are described in U.S. Pat. No. 4,798,603 to Meyer, et al.; U.S. Pat. No. 5,176,668 to Bernardin; U.S. Pat. No. 5,176,672 to Bruemmer. et al.; U.S. Pat. No. 5,192,606 to Proxmire, et al.; and U.S. Pat. No. 5,509,915 to Hanson, et al., which are incorporated herein in their entirety by reference thereto for all purposes. Several examples of absorbent articles are described in U.S. Pat. No. 5,649,916 to DiPalma. et al.; U.S. Pat. No. 6,110,158 to Kielpikowski; U.S. Pat. No. 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al., all of which are incorporated herein in their entirety by reference thereto for all purposes.

Of course, the elastic material is versatile and may also be incorporated into a wide variety of other types of articles. For example, the elastic material may be incorporated into a medical garment, such as gowns, caps, drapes, gloves, facemasks, etc.; industrial workwear garment, such as laboratory coats, coveralls, etc.; and so forth.

EXAMPLE 1

Fragrance releasing microcapsules were applied to five different nonwoven web laminates. Each sample was cut into 1 inch strips in its extensible direction. The laminate samples were as follows:
1. MD-Necked spunbond polypropylene nonwoven web thermally point bonded to an elastomeric film
2. CD-necked spunbond polypropylene nonwoven web with an elastomeric film extrusion coated thereon (non-point bonded)
3. MD-extensible spunbond attached to an elastomeric film via vertical fiber lamination (VFL)
4. Neck-bonded laminate (NBL)

Fragrance releasing microcapsules obtained from Scentisphere, LLC (Valhalla, N.Y.) were added to an aqueous ink composition containing a binder was applied to each sample. The ink was provided from Scentisphere, LLC. The fragrance releasing microcapsules were incorporated into the ink composition at about 10% by weight. The aqueous ink composition was applied to the nonwoven side of each sample using a no. 4 artist brush purchased from Princeton Art & Brush Co, to simulate flexographic printing. The print size was 1 inch× ½ inch long. Due to the low viscosity of the ink composition, the ink composition and the fragrance releasing microcapsules saturated the web upon application.

EXAMPLE 2

An elastic adhesive containing fragrance releasing microcapsules was prepared from by combining 0.1 gram of dry fragrance releasing microcapsules with 1 gram of rubber cement. The combination was mixed until the fragrance releasing microcapsules were substantially homogeneously distributed. Then, the mixture was applied to a 0.6 osy (ounce/sq. yard) necked polypropylene spunbond web. The mixture was applied to a target area of 0.5 inches×2 inches long. The mixture was applied using a scraper to simulate a slot coating system. The material was then folded over itself, which produced a necked bonded laminate-like (NBL-like) material. The laminate was lightly pressed to push the rubber cement mixture into the internal fibrous structure of the spunbond web.

FIGS. 5-10 are pictures taken with a scanning electron microscope. As shown in the pictures, the microcapsules are distributed within the internal fibrous structure of the web.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article comprising an absorbent core positioned between a substantially liquid-impermeable layer and a liquid-permeable layer, the absorbent article further comprising an elastic region, the elastic region comprising an elastic laminate comprising a nonwoven web facing laminated to an elastic material, wherein the nonwoven web facing has an internal fibrous structure having a thickness in a Z-direction, and wherein fragrance releasing microcapsules are randomly embedded inside the internal structure of the nonwoven web facing such that the elastic laminate releases fragrance after a stretching force has been applied to the nonwoven web facing, wherein the elastic region is selected from the group consisting of waistbands, leg/cuff gasketing, ears, side panels, outer covers, and combinations thereof.

2. An absorbent article as in claim 1, wherein a binder composition secures the fragrance releasing microcapsules within the internal fibrous structure of the nonwoven web facing.

3. An absorbent article as in claim 2, wherein the binder composition comprises an adhesive.

4. An absorbent article as in claim 2, wherein the add-on level of the binder composition and fragrance releasing microcapsules is at least about 2%.

5. An absorbent article as in claim 2, wherein the add-on level of the binder composition and fragrance releasing microcapsules is from about 4% to about 20%.

6. An absorbent article as in claim 2, wherein the binder composition contains from about 10% by weight to about 80% by weight of fragrance releasing microcapsules.

7. An absorbent article as in claim 1, wherein the elastic material is a film, strands, an elastic web, or a combination thereof.

8. An absorbent article as in claim 1, wherein the fragrance releasing microcapsules have an average diameter of between about 1 micrometer and about 50 micrometers.

9. An absorbent article as in claim 1 further comprising a second nonwoven web.

10. An absorbent article as in claim 1, wherein the nonwoven web facing comprises a meltblown web, a spunbond web, or a combination thereof.

11. An absorbent article as in claim 1, wherein the fragrance releasing microcapsules comprise a fragrance oil.

12. An absorbent article as in claim 11, wherein the fragrance oil is encapsulated within a capsule shell.

13. A method of forming an absorbent article comprising an elastic laminate as in claim 1 comprising:
providing a nonwoven web defining an internal fibrous structure having a thickness in a Z-direction;
applying a binder composition to the nonwoven web such that the binder composition enters the internal fibrous structure of the nonwoven web, wherein the binder composition comprises fragrance releasing microcapsules randomly embedded inside the internal fibrous structure of the nonwoven web;

thereafter, laminating the nonwoven web to an elastic material to form an elastic laminate such that the elastic laminate releases fragrance after a stretching force has been applied to the nonwoven web; and incorporating the elastic laminate into an absorbent article.

14. A method as in claim 13, wherein the nonwoven web is necked prior to laminating to the elastic material.

15. A method as in claim 13, wherein the nonwoven is stretched prior to application of the binder composition and prior to lamination to the elastic material.

16. A method as in claim 13, wherein the fragrance releasing microcapsules have an average diameter of between about 1 micrometer and about 50 micrometers.

17. A method as in claim 13, wherein the binder composition has a viscosity of less than about 100 cP, measured with a Brookfield viscometer, type DV-I or LV-IV, at 60 rpm and 20° C.

18. A method as in claim 13, wherein the binder composition and fragrance releasing microcapsules are applied to the nonwoven web at an add-on level of at least about 2%.

19. A method as in claim 13, wherein the binder composition and fragrance releasing microcapsules are applied to the nonwoven web at an add-on level of from about 4% to about 20%.

20. A method as in claim 13, wherein the binder composition contains from about 10% by weight to about 80% by weight of fragrance releasing microcapsules.

21. A method as in claim 13, further comprising the step of pressing the nonwoven web in a nip to force the fragrance releasing microcapsules into the internal fibrous structure of the nonwoven web, wherein the nip exerts a pressure of less than about 25 psi on the nonwoven web.

22. An absorbent article as in claim 1, wherein the absorbent article is a personal care absorbent article.

23. An absorbent article as in claim 22, wherein the personal care absorbent article is selected from the group consisting of diapers, training pants, and incontinence articles.

24. An absorbent article as in claim 1, wherein the fragrance releasing microcapsules consists of a fragrance composition encapsulated within a capsule shell.

* * * * *